United States Patent
Lecoupeau et al.

(10) Patent No.: US 7,368,144 B2
(45) Date of Patent: May 6, 2008

(54) METHOD FOR OBTAINING COCOA BEAN POLYPHENOL EXTRACTS, RESULTING EXTRACTS AND USES THEREOF

(75) Inventors: Jean-Paul Lecoupeau, Venables (FR); Joseph Vercauteren, Castelnau-le-Lez (FR)

(73) Assignee: Barry Callebaut France, Meulan (FR)

( * ) Notice: Subject to any disclaimer, the term of this patent is extended or adjusted under 35 U.S.C. 154(b) by 482 days.

(21) Appl. No.: 10/344,250

(22) PCT Filed: Aug. 10, 2001

(86) PCT No.: PCT/FR01/02605

§ 371 (c)(1),
(2), (4) Date: Jul. 16, 2003

(87) PCT Pub. No.: WO02/14251

PCT Pub. Date: Feb. 21, 2002

(65) Prior Publication Data

US 2004/0096566 A1    May 20, 2004

(30) Foreign Application Priority Data

Aug. 11, 2000 (FR) .................................. 00 10603

(51) Int. Cl.
*A23L 1/28*    (2006.01)

(52) U.S. Cl. ...................... 426/655; 426/631; 426/492; 426/430

(58) Field of Classification Search ................ 426/655, 426/631, 492, 430
See application file for complete search history.

(56) References Cited

U.S. PATENT DOCUMENTS

| 2,380,158 | A | 7/1945 | Durrenmatt et al. |
| 4,352,746 | A | 10/1982 | Rehacek et al. |
| 4,532,147 | A | 7/1985 | Jonas et al. |
| 4,970,090 | A | 11/1990 | Zeiger et al. |
| 5,554,645 | A | 9/1996 | Romanczyk, Jr. et al. |
| 6,015,913 | A | 1/2000 | Hammerstone et al. |
| 6,265,593 | B1 * | 7/2001 | Best et al. ................ 554/12 |

(Continued)

FOREIGN PATENT DOCUMENTS

CA          840382         4/1970

(Continued)

OTHER PUBLICATIONS

Patent Abstracts of Japan; vol. 1998, No. 1, Jan. 30, 1998 & JP 09 234018; Sep. 9, 1997.

(Continued)

*Primary Examiner*—Anthony Weier
(74) *Attorney, Agent, or Firm*—Thomas Hoxie; Arthur Yang; Hoxie & Associates LLC

(57) ABSTRACT

The invention concerns a method for obtaining extracts based on polyphenol compounds contained in cocoa, characterised in that it includes: using fresh beans, which have not been pre-treated or defatted, said fresh beans whereof their pulp and shell have been eliminated, so as to obtain clean almonds; grinding said almonds, in the presence of solvent(s); macerating the ground almonds in conditions enabling extraction of the desired compounds; filtering the macerated mixture; recuperating an extract containing said compounds from the filtrate. The invention also concerns the extracts and their uses for cosmetic, food and therapeutic purposes.

6 Claims, 2 Drawing Sheets

U.S. PATENT DOCUMENTS

Figure 1:
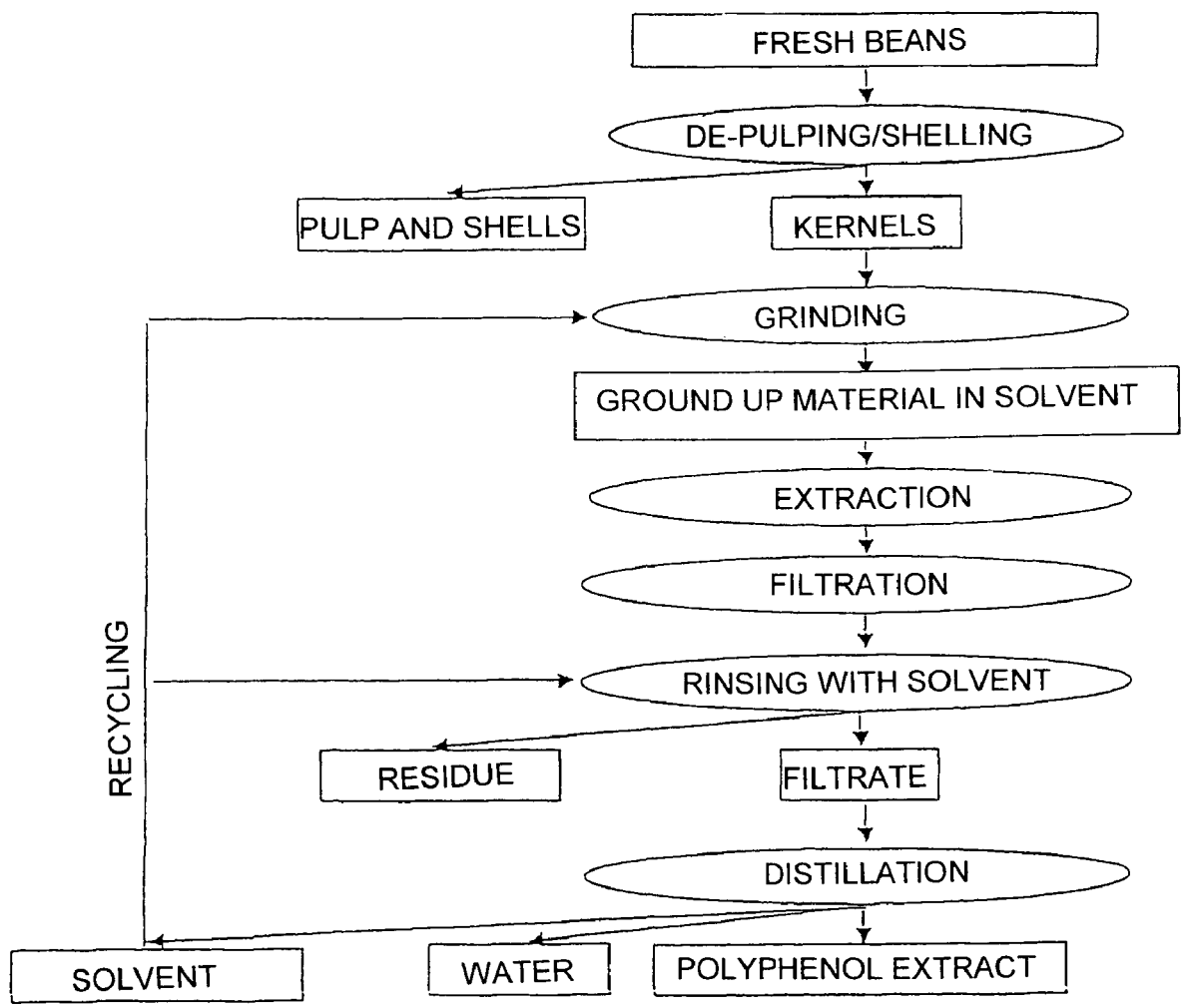

| | | |
|---|---|---|
| 6,426,080 B1 | 7/2002 | Golz-Berner et al. |
| 6,524,595 B1 | 2/2003 | Perrier et al. |
| 2002/0022040 A1 | 2/2002 | Robinson et al. |
| 2002/0098213 A1 | 7/2002 | Bonte et al. |
| 2002/0106388 A1 | 8/2002 | Pugliese |
| 2004/0166142 A1* | 8/2004 | Chevaux et al. ............ 424/439 |

FOREIGN PATENT DOCUMENTS

| | | |
|---|---|---|
| DE | 2055030 | 5/1972 |
| EP | 0 344 728 | 5/1989 |
| EP | 0 393 362 | 3/1990 |
| EP | 0 906 761 | 4/1999 |
| EP | 0 943 675 | 9/1999 |
| EP | 1 026 164 | 8/2000 |
| ES | 2 099 676 | 5/1997 |
| FR | 2 609 395 | 7/1998 |
| FR | 2818095 * | 6/2002 |
| GB | 14624 | 7/1897 |
| GB | 341000 | 1/1931 |
| GB | 345250 | 3/1931 |
| GB | 562123 | 6/1944 |
| GB | 751121 | 6/1956 |
| GB | 2 223 944 | 4/1990 |
| JP | 57-206391 | 12/1982 |
| JP | 61-239872 * | 10/1986 |
| JP | 3-94640 * | 4/1991 |
| WO | WO 96/10387 | 4/1996 |
| WO | WO 96/10404 | 4/1996 |
| WO | WO 97/36497 | 10/1997 |
| WO | WO 97 36597 | 10/1997 |
| WO | WO 98/47534 | 10/1998 |
| WO | WO 99 45788 | 9/1999 |
| WO | WO99/65322 | 12/1999 |
| WO | WO 00/01351 | 1/2000 |
| WO | WO 01/93690 | 1/2001 |
| WO | WO 02/13838 | 2/2002 |

OTHER PUBLICATIONS

Patent Abstracts of Japan; vol. 2000, No. 2, Feb. 29, 2000 & JP 11 308978; Nov. 9, 1999.

Patent Abstracts of Japan; vol. 1998, No. 1, Jan. 30, 1998 & JP 09 224606; Sep. 2, 1997.

Patent Abstracts of Japan; vol. 1996, No. 2, Jun. 29, 1996 & JP 07 274894; Oct. 24, 1995.

Patent Abstracts of Japan; vol. 1995, No. 11, Dec. 26, 1995 & JP 07 213251; Aug. 15, 1995.

Patent Abstracts of Japan; vol. 18, No. 427, Aug. 10, 1994 & JP 06 128164; May 10, 1994.

Ahmad, F. et al. *Insulin like activity in (-) epicatechin*, Acta Diabetologica Latina, 1989, pp. 291-300, vol. 26, No. 4 (Abstract).

Bastide, P. et al. *Changes in phenolic compounds of the Theobroma cacao bean during fruit growth and maturation*, Bulletin de liaison—Groupe Polyphenols, 1986, pp. 425-427, vol. 13 (Abstract).

Chakraborty, A. et al. *Evaluation of biological activities of Rhus aromaticae extracts*, Pharmaceutical and Pharmacological Letters, 2000, pp. 76-81, vol. 10, No. 2 (Abstract).

Chevaux, K. A. et al. *Proximate, Mineral and Procyanidin Content of Certain Foods and Beverages Consumed by the Kuna Amerinds of Panama*, Journal of Food Composition and Analysis, 2001, pp. 553-563, vol. 14, No. 6 (Abstract).

Gebhardt, R. et al. *Antioxidant and hepatoprotective effects of artichoke extracts and constituents in cultured rat hepatocytes*, Toxicology in Vitro, 1997, pp. 669-672, vol. 11, No. 5 (Abstract).

Halder, J. et al. *Protective Role of Black Tea against Oxidative Damage of Human Red Blood Cells*, Biochemical and Biophysical Research Communications, 1998, pp. 903-907, vol. 244, No. 3.

Hirano, R. et al. *Antioxidant effects of polyphenols in chocolate on low-density lipoprotein both in vitro and ex vivo*, Journal of Nutritional Science and Vitaminology, 2000, pp. 199-204, vol. 46, No. 4 (Abstract).

Ogasawara H. et al. *The role of hydrogen peroxide in basophil histamine release and the effect of selected flavonoids*, Journal of Allergy and Clinical Immunology, 1986, pp. 321-328, vol. 78, No. 2 (Abstract).

Osakabe, N. et al. *Effects of Polyphenol Substances Derived from Theobroma cacao on Gastric Mucosal Lesion Induced by Ethanol*, Bioscience, Biotechnology and Biochemistry, 1998, pp. 1535-1538, vol. 62, No. 8.

Sanz, M.J. et al. *Influence of a series of natural flavonoids on free radical generating systems and oxidative stress*, Xenobiotica, 1994, pp. 689-699, vol. 24, No. 7 (Abstract).

Wan, Y. et al. *Effects of cocoa powder and dark chocolate on LDL oxidative susceptibility and prostaglandin concentrations in humans*, American Journal of Clinical Nutrition, 2001, pp. 596-602, vol. 74, No. 5.

Yoneda, T. et al. *Antioxidant effects of "beta catechin"*, Biochemistry and Molecular Biology International, 1995, pp. 995-1008, vol. 35, No. 5 (Abstract).

Zhang, A. et al. *Inhibitory effects of jasmine green tea epicatechin isomers on free radical-induced lysis of red blood cells*, Life Sciences, 1997, pp. 383-394, vol. 61, No. 4 (Abstract).

Zhang, J. et al. *Antioxidant Activities of Baicalin, Green Tea Polyphenols and Alizarin in vitro and in vivo*, Journal of Nutritional & Environmental Medicine, pp. 79-90, vol. 7, No. 2 (Abstract), 1997.

* cited by examiner

METHOD FOR OBTAINING COCOA BEAN POLYPHENOL EXTRACTS, RESULTING EXTRACTS AND USES THEREOF

The present application is a 371 U.S. national phase of PCT/FR01/02605, filed 10 Aug. 2001, which designated the U.S.

The present invention relates to a process for obtaining extracts based on polyphenol compounds from cocoa beans, the extracts obtained and their uses.

It is known that the fresh cocoa bean contains approximately 40% water, 30 to 35% lipids, 4 to 6% polyphenols or polyphenol derivatives, 1.5% xanthines, the rest being mainly constituted by proteins, starch, cellulose and sugars. In this respect, reference may be made to the following articles:

"Cacao procyandins: major flavanoids and identification of some minor metabolites" by L. J. Porter, Z. Ma and B. G. Chan, published in Phytochemistry vol. 35, No. 5 p1657-1663, 1991 and Epicatechin content in fermented and unfermented cocoa beans" by H. Kim and P. G. Keeney, published in Journal of Food Science—vol. 49 (1984) p 1090-1092.

It will be noted that the term "polyphenol", as used in the description and the claims designates polyphenols which are non-substituted, and substituted in particular in the form of glycosides. These polyphenols belong in particular to the class of anthocyanines, flavonoids and flavanols and their oligomers, of A and/or B types.

Similarly, it will be noted that the term lipid or fatty matter represents free fatty acids, sterols, in particular phytosterols and mono-, di- and triglicerides.

By pre-treatment is meant an operation of fermentation and/or drying and/or washing.

It is known that cocoa originates from South America and that its fruits or pods are picked, the beans undergo a pre-treatment which consists of fermenting for five to six days before being dried. During this fermentation, a certain number of biochemical reactions occur, which translate, in particular, by the destruction of pathogenic micro-organisms, into the formation of aroma precursors and a partial degradation of polyphenols following enzymatic oxidation or tanning of proteins. It is considered that 70 to 80% of polyphenols are degraded during fermentation.

The polyphenols are the most powerful natural anti-oxidant and anti-radical substances known. Polyphenol extracts and preparations which contain them are usually used in the following indications: circulatory disorders, venous-lymphatic insufficiency, cutaneous capillary fragility, retinal circulatory disorders, haemorrhoids, rashes caused by the sun or associated with the effect of radiation (prevention of damage caused by radiotherapy), hypertension, hypercholesterolemia, various viral and microbial illnesses. Over the last few years, numerous publications have revealed types of action at a molecular level by which they are capable of fighting major illnesses which are:

Cardiovascular diseases:
  Platelet antiaggregates (Petroni, A., M. Blasevich, M. Salami, N. Papini, G. F. Montedoro and C. Galli, *Inhibition of platelet aggregation and eicosanoid production by phenolic components of olive oil*. Thromb Res, 1995. 78(2): p.151-160)
  Anti-inflammatories and protectors against the oxidation of LDL-cholesterols (Frankel, E., J. Kanner, J. German, E. Parks and J. Kinsella, *Inhibition of oxidation of human low-density lipoprotein by phenolic substances in red wine*. Lancet, 1993. 341 (8843): p. 454-457).
  Protector against the oxidation of eicosanoids (Pace-Asciak, C. R., S. Hahn, E. P. Diamandis, G. Soleas and D. M. Goldberg, *The red wine phenolics transresveratrol and quercetin block human platelet aggregation and eicosanoid synthesis: implications for protection against coronary heart disease*. Clin Chim Acta, 1995. 235(2): p. 207-219)
  Anti-atherosclerotics (Yamakoshi, J., S. Kataoka, T. Koga and T. Ariga, *Proanthocyanidin-rich extract from grape seeds attenuates the development of aortic atherosclerosis in cholesterol-fed rabbits*. Atherosclerosis, 1999. 142(1): p. 139-149)
  Anti-thrombotics (Fuhrman, B., A. Lavy and M. Aviram, *Consumption of red wine with meals reduces the susceptibility of human plasma and low-density lipoprotein to lipid peroxidation*. Am J Clin Nutr, 1995. 61(3): p. 549-554)
Alzheimers (Orgogozo, J. M., J. F. Dartigues, S. Lafont, L. Letenneur, D. Commenges, R. Salamon, S. Renaud and M. Breteler, *Wine consumption and dementia in the elderly: A prospective community study in the Bordeaux area*. Rev Neurol, 1997. 153(3): p. 185-192)
Cancer (Jang, M. S., E. N. Cai, G. O. Udeani, K. V. Slowing, C. F. Thomas, C. W. W. Beecher, H. H. S. Fong, N. R. Farnsworth, A. D. Kinghorn, R. G. Mehta, R. C. Moon and J. M. Pezzuto, *Cancer chemopreventive activity of resveratrol, a natural product derived from grapes*. Science, 1997. 275(5297): p. 218-220)

Taking into account the fact that cocoa contains polyphenols and of the importance of the use of polyphenols in the medical field, this has led to an attempt to extract from the cocoa, the polyphenol compounds that it contains in particular with the aim of creating dietetic food and drinks containing this antioxidant. A pre-treatment comprising fermentation followed by a drying operation constitutes a major drawback in the sense that it reduces the extraction yield of polyphenols contained in the cocoa.

In seeking to overcome these drawbacks, the inventors have discovered that the use of beans not having undergone a prior treatment and carrying out the extraction under specific conditions would make it possible to obtain extracts of original composition, endowed with very useful properties.

An aim of the invention is therefore to provide a process for the extraction of cocoa beans making it possible to have available extracts with a high polyphenol content and enriched, (in comparison to the initial content of the beans) with certain useful lipid derivatives. It also aims to provide such extracts as new products.

The invention moreover aims to use to advantage properties or extracts in various applications, in particular in the food, cosmetic and therapeutic field.

The process, according to the invention, for obtaining extracts based on polyphenol compounds, starting from cocoa beans, is characterised in that it comprises
  the use of fresh beans, not having undergone a pre-treatment, or defatting, these beans having had their pulp and shell removed, in such a way as to obtain clean kernels,
  the grinding of said kernels, in the presence of a solvent,
  the maceration of the ground kernels under conditions allowing the sought compounds to be extracted, the filtration of the maceration mixture, the recovery of the extract containing said compounds from the filtrate.

The beans used are pre-treated or not pre-treated.

According to a variant of the present invention, commercial cocoa beans are used, i.e. beans having undergone a pre-treatment comprising drying, the kernels of which are rehumidified before grinding, for example with 30 to 50% warm water.

The maceration stage is carried out using water or a mixture of water and several solvents, capable of solubilising the polyphenols and lipids, without altering their properties, such as ethanol, acetone, 2-butanol and 2-propanol. Preferably, the solvent content is greater than 50% by volume.

The operation is advantageously carried out at a temperature of the order of 20 to 50° C., over one hour to several days.

As the examples show, a maceration of only 1 hour, with a solvent such as 70° ethanol makes it possible to obtain very high quality extracts, which is very useful for the industrial applications of the process.

The mixture obtained is then filtered and the filtrate is treated to recover the sought extract.

Advantageously the filtration cake is subjected beforehand to one or more washing stages. The same solvent as that used in the maceration stage is in particular used.

Recovery of the extract based on polyphenol compounds consists in particular of distillation, carried out so as to evaporate the solvent and obtain an extract.

The extracts obtained have the advantage of an increased content of polyphenol compounds and an enrichment, relative to the composition of the initial beans, of phytosterols, in particular β-sitosterol.

Such extracts constitute new products and, as such are also within the scope of the invention.

The invention relates in particular to extracts characterised by a content (% in weight relative to the total extract) of 15 to 65% polyphenols, from 0 to 11% lipids and from 0 to 20% xanthines.

The invention relates in particular to the extracts in which the lipids comprise from 10 to 30% by weight of polysterols with preferably 7 to 15% β-sitosterol. This preferential content is achieved when the process according to the invention is implemented on fresh beans.

Such original extracts advantageously constitute a signature of the process of the invention.

The properties highlighted in the polyphenols have already been indicated at the beginning of the description. Similarly, the phystosterols constitute products of great usefulness.

Oxidized phytosterols are phytonutrients the nutritional qualities of which in public health are particularly well documented. A number of scientific works have shown the role, in particular of β-sitosterol in the protection against and the prevention of certain diseases.

These qualities can be summarized in the following way:
a stimulating effect on the immune system by increasing the immunological defences against viral and bacterial infections (Bouic, P. J. D. et al. International Journal of Immunopharmacology, vol. 18, no. 12, p. 693-700, December 1996),
a hypocholesterolemia effect in man without a change of diet or modification of physical activity (Métab. Clin. Exper., vol. 38, p. 136-40 (1989); American J. Clin. Nutr., vol. 59, p. 1325-31 (1994)),
combating disorders linked to stress (immunosuppression, pains and neuralgias etc.), P. J. D. Bouic et al: International Journal of Sports Medicine, 1999,
combating prostate diseases, Klippel K. F. et al: British Journal of Urology, v. 80 (3), pp. 427-432, September 1997,
combating cancer of the prostate and of the breast,
combating certain autoimmune diseases such as Lupus, Psoriasis, Chronic fatigue syndrome as well as rhumatoid polyarthritis, (P. J. D. Bouic: Newsletter of the Arthritis Trust of America, Summer 1998),
maintaining a certain level of lymphocytes in patients suffering from AIDS and therefore prolonging their life (Bouic, P. J. D. AIDS Bulletin, v.6 #3, p 18-20, September 1997), and,
an anti-diabetic, antihyperglycemic effect (M. D. Ivorra et al: Archives of the International Pharmacodyn, v. 296, pp. 224-231, April 1988) as well as an anti-ulcer, anti-inflammatory and anti-pyretic effect (M. B. Gupta et al: Planta medica (Journal of Medicinal Plant Research) vol. 39, p 157-163, 1980).

The extracts according to the invention, because of their composition, therefore present, a wide spectrum of activity and can be used in numerous application fields.

The use of the extracts according to the invention in the field of foodstuffs can in particular be mentioned. These extracts in fact constitute high value added additives.

They are suitable, in particular, for supplementing, for example, chocolates, drinks, dairy products.

The use of extracts according to the invention will thus be cited as additives to certain foods to produce real healthfoods (also called functional foods or nutraceuticals) for which the health claims ensue from all of the biological properties that they are known for.

The invention also applies to nutritional supplements containing an effective quantity of extracts according to the invention.

In particular, the nutritional supplements according to the invention comprise at least one extract according to the invention at the rate of 25 to 300 mg, preferably 100 to 200 mg.

Their administration by oral route, in the form of tablets, capsules, gelatin capsules is particularly suitable.

The extracts according to the invention are also particularly useful in the cosmetic field, where their properties are advantageously used to advantage in the composition of formulations, as active ingredients, or combined with other active ingredients.

Such cosmetic compositions are therefore characterised in that they contain an effective quantity, for a cosmetological use, of the extracts of the invention, in combination with the vehicles usually used in cosmetology. These extracts will therefore be used in the development of creams, lotions, mousses, soaps and others.

The properties of the extracts according to the invention also give them significant usefulness in therapeutics. As indicated above, study of the pharmacological properties of their constituents has shown their effectiveness in various diseases. These properties are accompanied moreover, by the great innocuousness of these products, which therefore have a particularly satisfying therapeutic index.

The invention therefore relates to the use of the extract according to the invention as the source of choice for obtaining active ingredients intended for pharmaceutical use.

Figure 2:
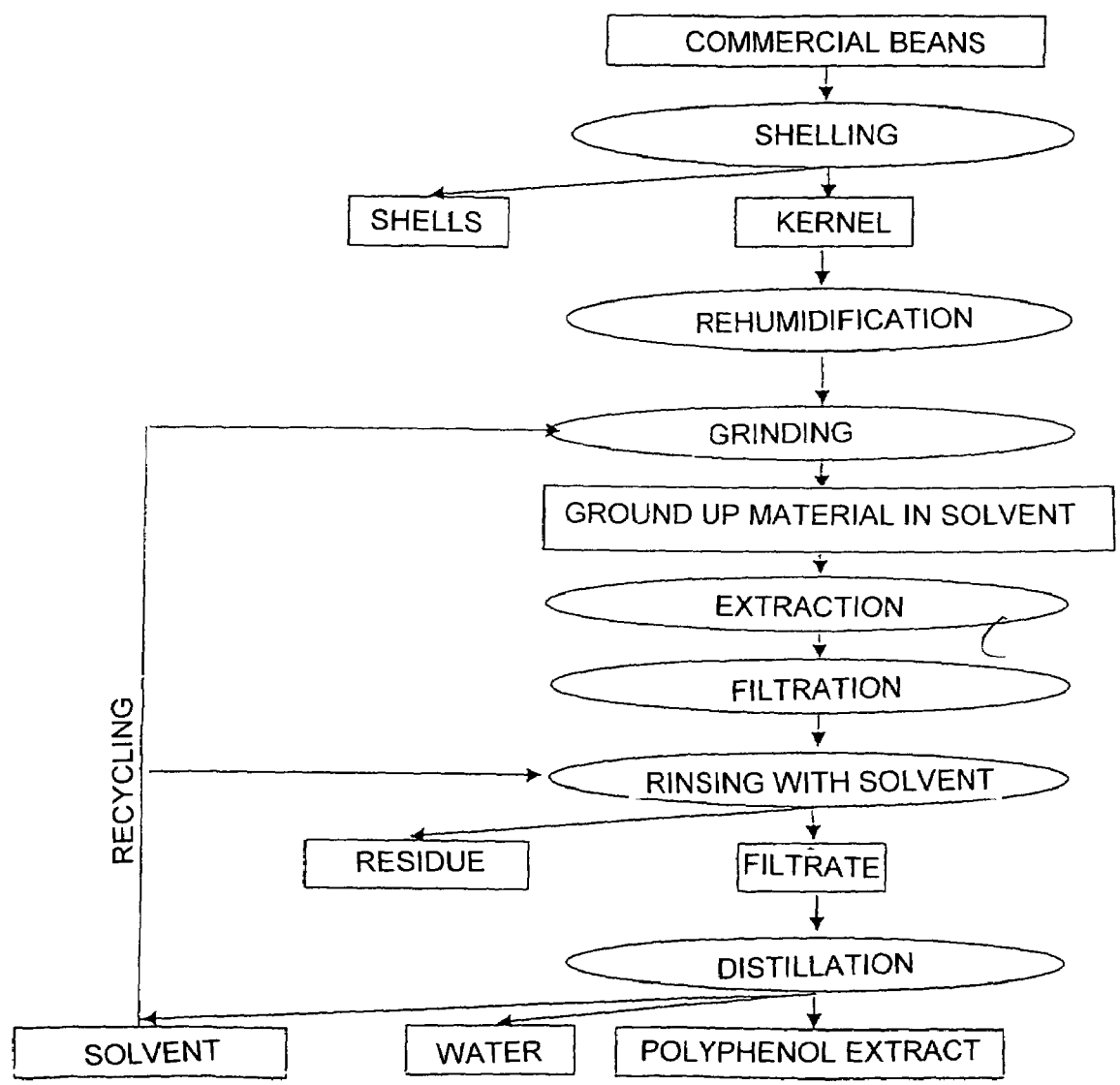

Other characteristics and advantages of the present invention will become apparent from the description given below with reference to the attached drawings which illustrate two examples of implementation which are not limiting in any way. In the drawings:

FIG. 1 is a diagram representing the successive stages of the process which is a subject of the invention, and, FIG. 2 is a diagram similar to that of FIG. 1 illustrating the variant of the process of the invention according to which commercial cocoa beans are used the kernels of which are rehumidified before undergoing the grinding operations in an extraction and distillation solvent.

FIG. 1 is referred to first.

According to the invention, the fresh beans, pre-treated or not pre-treated, have the pulp and the shell removed by a pulp removal and shelling operation, for example using an "industrial peeling machine" type device. Clean kernels are thus obtained which are ground, for example in a cutting mill, in the presence of a solvent. As specified above, this solvent is advantageously chosen from the group comprising in particular water, ethanol, acetone, 2-butanol, 2-propanol, in all proportions, mixed with water. Preferably, the solvent content is greater than 50% by volume (taking into account the water contributed by the beans).

The ground kernel/solvent mixture can be left to infuse from a few hours to several days and can be either hot or cold. If this infusion is carried out hot, temperatures which are too high should be avoided (i.e. greater than 60° C.), in order to limit chemical oxidation and chemical degradation of the compounds to be extracted.

The mixture is then filtered and rinsed several times using the solvent employed.

Distillation is then carried out with a view to obtaining an extract.

This distillation is preferably carried out at a temperature of 50 to 60° C. in order to avoid degradation of the polyphenol compounds, under a residual pressure of 12 to 20 Kpa, with a view to evaporating the mixture of solvents contained in the filtrate. As indicated in the diagram in FIG. 1, the solvent recovered during the distillation stage of the filtrate can be recycled in the grinding stage of the kernels.

The variant of the process illustrated by FIG. 2 differs from the process described above with reference to FIG. 1 only by the fact that the process is implemented starting from commercial cocoa beans, i.e. beans having undergone a pre-treatment comprising drying, the kernels thus obtained being then subjected to a rehumidification stage after shelling, this stage being carried out with 30 to 50% warm water, before the grinding stage in the solvent. Such rehumidification allows the cell walls of the kernels to regain their elasticity and to therefore not be ruptured during grinding in the presence of the solvent. The percentage of lipids extracted is in this case higher than with fresh non-rehumidified beans.

Examples of extracts resulting from the implementation of the process which is a subject of the invention are given below.

In these examples, xanthines represent threobromine and caffeine,

It will be noted that the percentages of polyphenols are expressed as gallic acid equivalents, according to the FOLIN CIOCALTEU method.

The anti-radicular activity was evaluated according to the DPPH test (1,1diphenyl-2-picryl-hydroxy radical). It is necessary to know the molar concentration of the extract solutions subjected to the test. Now, the nature of all of the molecules present not being known, an "estimate" of an average molecular weight (that of catechin) is chosen (arbitrarily) to express this molarity. The results are then expressed by the number of micromoles necessary to reduce 50% of the radical forms of DPPH. From which, the greater the value, the less the extract is anti-radicular.

The percentage of extract/dry material (extract expressed over the dry material) is determined using the following relationship:

$$\% \text{ Extract/dry material} = \frac{10\,000 * E}{W * (100 - H)}$$

Where:
E designates the weight of the extract in grams,
W designates the weight of the beans in grams, and,
H designates the level of humidity of the beans.

This relationship allows the results obtained from beans of different origins to be compared. In fact, the humidity level of a bean is variable according to its origin.

Assay of the xanthines was carried out according to OICCC method No. 107 (1998).

The fat composition was determined using the C. C Young method (see "*The interpretation of GLC Triglycerides Data for the determination of Cocoa Butter Equivalents in chocolate. A new approach.*" 1984, JAOCS, 61, p 576-581). The exploitation of the results according to PADLEY makes it possible to interpret the composition of the lipid part (fatty acid, sterols, triglycerides etc. ) of the extract.

1) Extraction according to the invention:

| | Variation of the extraction yields according to the type of solvent (maceration for 24 hours) | | | | | | |
|---|---|---|---|---|---|---|---|
| | Cold Water | MeOH 70% | Water at 60° C. | Acetone (70%) | 2-propanol (70%) | Ethanol (70%) | 2-butanol (70%) |
| % extract/ dry material | 8.8 | 10.6 | 13.4 | 12 | 14.4 | 11.1 | 10.1 |
| | | | Extract composition (%) | | | | |
| Lipids | 0.6 | 0 | 8.7 | 0.1 | 3.6 | 3.5 | 10.4 |
| Xanthines | 8.6 | 6 | 9.4 | 5.6 | 9.9 | 8.5 | 16.1 |
| Polyphenols | 17.2 | 41.2 | 19.1 | 61.1 | 45.5 | 54.3 | 37.6 |
| DPPH activity | 88.5 | 36.4 | 147.6 | 25.9 | 39 | 31.2 | 41.6 |

The extract containing the most useful lipid fraction combined with the best anti-radicular activity (due to the polyphenol fraction) is obtained by the ethanol-water solvent mixture (70:30 by volume).

This solvent is therefore preferentially chosen.

2) Comparison of extractions from beans originating from the Ivory Coast and from Cameroon The comparison is carried out on the sterol content of the fatty matter contained in the extracts of the invention.

It should be recalled that the composition of the fatty matter of the fresh bean varies little from one origin to another. The percentage of sterols in cocoa butter is from 0.14 to 0.16%, whilst the percentage of β-sitosterol is from 0.08 to 0.1%.

In the table below, the extractions are carried out on beans from Cameroon with 70% ethanol.

|  | 1 hour | 2 hours | 4 hours | 16 hours | 2 days |
|---|---|---|---|---|---|
| % Fatty acids | 1.72 | 1.24 | 1.10 | 1.58 | 2.67 |
| % Total sterols | 15.59 | 20.44 | 24.80 | 25.16 | 25.60 |
| % β-sitosterol | 9.75 | 12.67 | 14.63 | 14.59 | 14.87 |
| % Diglycerides | 79.91 | 75.65 | 63.12 | 72.20 | 68.73 |
| % Triglycerides | 2.76 | 2.65 | 2.11 | 1.04 | 2.98 |

In the table below, the extractions are carried out on beans from the Ivory Coast with 70% ethanol.

|  | 1 hour | 2 hours | 4 hours | 16 hours | 2 days |
|---|---|---|---|---|---|
| % Fatty acids | 11.79 | 15.30 | 14.47 | 18.02 | 17.62 |
| % Total sterols | 19.82 | 17.68 | 20.30 | 20.74 | 20.97 |
| % β-sitosterol | 11.54 | 10.51 | 11.95 | 12.18 | 12.18 |
| % Diglycerides | 62.03 | 61.41 | 59.80 | 55.42 | 56.25 |
| % Triglycerides | 3.86 | 2.00 | 1.70 | 0.99 | 1.20 |

It will be noted that the process according to the invention makes it possible to enrich the lipid fraction with sterols and, in particular, with β-sitosterol, relative to cocoa butter.

3) Comparison of extractions according to the origin of the cocoa beans (maceration for 24 hours)

|  | Cameroon | Equatorial Guinea | Ivory Coast | Brazil |
|---|---|---|---|---|
| Extraction with 70% ethanol. | | | | |
| % extract/dry material | 11.1 | 9.5 | 8.4 | 12 |
| Extract composition % | | | | |
| Lipids | 3.5 | 4.9 | 9.2 | 3.4 |
| Xanthines | 8.5 | 8.3 | 10.4 | 14.2 |
| Polyphenols | 54.3 | 40.2 | 47.6 | 38.2 |
| DPPH activity | 31.2 | 42 | 47.9 | 40.6 |

4) Extraction from commercial beans (maceration for 24 hours)

| | Ivory Coast |
|---|---|
| Extraction with 70% ethanol. | |
| % extract/dry material | 9.4 |
| Extract composition (%) | |
| Lipids | 9.5 |
| Xanthines | 10.5 |
| Polyphenols | 19 |
| Anti-radicular activity | 99 |

5) Composition in the agro/foodstuffs field

Non-limiting examples of the use of extracts according to the invention, obtained by the implementation of the process defined above are indicated below. These extracts can be used as a supplement in numerous food products. The applicant has tested the addition of extracts obtained with 70% ethanol, in chocolate-containing products. In all of the examples indicated below, a comparison was made between the product with added extracts and a product free from such an addition:

| DARK CHOCOLATE | |
|---|---|
| Composition: cocoa paste | 56% |
| Sugar | 26.99% |
| Cocoa butter | 16% |
| Vanilla | 0.01% |
| Extract of the invention | 1% |

Tasting: the jury was composed of 18 people: 12 people out of 18 preferred the chocolate with the addition of extract according to the invention. It was found to be more rounded in flavour and more aromatic.

| MILK CHOCOLATE | |
|---|---|
| Composition: cocoa paste | 7.60% |
| Sugar | 41.30% |
| Cocoa butter | 27.50% |
| Full-fat milk | 22.50% |
| Lecithin | 0.59% |
| Vanilla | 0.01% |
| Extract of the invention | 0.50% |

Tasting: the jury was composed of 15 people.

Result: slightly more pinkish colour; no significant difference was found as regards the taste of the product.

| PREPARATION OF DRINKS FOR AN AUTOMATIC VENDING MACHINE | |
|---|---|
| Sugar composition: | 52.69% |
| Fat-reduced cocoa powder | 14% |
| Vanillin | 0.01% |
| Milk (0% fat) | 33% |
| Extract of the invention | 0.30% |

Tasting: the jury was composed of 9 people.

200 ml of hot water was added to 25 grams of this preparation.

Result: no significant difference was found between the two preparations.

It remains understood of course that the present invention is not limited to the various examples of implementation mentioned above but that it encompasses all of the variants.

6) Composition in the cosmetic field

Cosmetic product, with sunscreen, to combat skin aging and to aid slimming.

A water/oil emulsion is created by mixing a sunscreen with the polyphenol extract from cocoa according to the invention and excipients for a cream. This serum combines sunscreen properties (by the presence of a sunscreen and polyphenols of the extract according to the invention), anti-wrinkle properties (by the presence of polyphenols of the extract according to the invention) and slimming properties (by the presence of xanthic bases of the extract according to the invention).

| Formulation: | |
|---|---|
| Isopropylmethoxycinnamate and ethyl diisopropylcinnamate (Neo Heliopan E 1000 ®) | 3% |
| Cocoa bean extract according to the invention | 3% |
| Excipients for W/O serum | S.Q. |
| Composition of the excipients: | |
| Propylene glycol dicaprylate/dicarate + stearalkonium hectorite + propylene carbonate (Miglyol 840 gel B ®) | 20.0% |
| Bis-diglyceryl caprylate/caprate/isostearate/hydroxystearate adipate (softisan 649 ®) | 5.0% |
| Isostearyl diglyceryl succinate (Imwitor 780 K ®) | 5.0% |
| Paraffin oil | 8.0% |
| Solid paraffin | 3.0% |
| Magnesium sulphate | 2.0% |
| Water | s.q. |
| | 100.0% |

The invention claimed is:

1. Process for obtaining a cocoa extract comprising a polyphenol compound and a lipid compound contained in cocoa, said process consisting essentially of:

obtaining kernels from fresh untreated beans, or dried beans which have not been defatted, said kernels having been obtained from said beans by removing the pulp and shell from said beans, crushing said kernels, in the presence of at least one solvent to produce crushed kernels, macerating the crushed kernels under conditions to extract said compounds in a maceration mixture, filtering said maceration mixture to obtain a filtrate, and recovering said extract from said filtrate.

2. Process according to claim 1, wherein the macerating further comprises admixing with at least one solvent capable of solubilizing polyphenol and lipid.

3. Process according to claim 2, wherein said at least one solvent comprises water or a mixture of water and solvent, the solvent being selected from the group consisting of ethanol, acetone, 2-butanol, and 2-propanol.

4. Process according to claim 2, wherein said at least one solvent is a solvent/water mixture, said mixture having a solvent content greater than 50% by volume.

5. Process according to claim 1, wherein said macerating is carried out for a period of over 1 hour to several days, optionally, under hot or cold conditions.

6. Process according to claim 1, wherein said recovering comprises distallation of the filtrate obtained, at a temperature ranging between 50 and 60° C., under a residual pressure of 12 to 20 Kpa.

* * * * *